United States Patent [19]

Hemberger et al.

[11] Patent Number: 5,583,111
[45] Date of Patent: Dec. 10, 1996

[54] THROMBIN INHIBITORS

[75] Inventors: Jürgen Hemberger, Aschaffenburg; Roy Sawyer, Dyfed; Sabine Wolf, Otzberg; Johannes Dodt, Recklinghausen, all of Germany

[73] Assignee: Merck Patent Gesellschaft Mit Beshrankter Haftung, Darmstadt, Germany

[21] Appl. No.: 362,567

[22] PCT Filed: May 3, 1994

[86] PCT No.: PCT/EP94/01404

§ 371 Date: Jan. 5, 1995

§ 102(e) Date: Jan. 5, 1995

[87] PCT Pub. No.: WO94/26777

PCT Pub. Date: Nov. 24, 1994

[30] Foreign Application Priority Data

May 7, 1993 [GB] United Kingdom ............ 9309509

[51] Int. Cl.$^6$ .................. A61K 38/16; A61K 35/62; C07K 1/36; C07K 14/815

[52] U.S. Cl. .................. 514/21; 530/300; 530/350; 530/413; 530/417; 530/855; 514/822; 424/537

[58] Field of Search ................ 530/300, 350, 530/413, 855, 417; 514/21, 822; 424/520, 537

[56] References Cited

U.S. PATENT DOCUMENTS

| 4,390,630 | 6/1983 | Sawyer et al. | 435/226 |
| 4,791,100 | 12/1988 | Kramer et al. | 514/12 |

FOREIGN PATENT DOCUMENTS

| 9005143 | 5/1990 | WIPO . |
| 9115576 | 10/1991 | WIPO . |

OTHER PUBLICATIONS

Harris et al. "Protein Purification Methods" pp. 57–64 & 245–257.

Primary Examiner—Mindy Fleisher
Assistant Examiner—Nancy J. Degen
Attorney, Agent, or Firm—Millen, White, Zelano, & Branigan, P.C.

[57] ABSTRACT

The invention relates to novel polypeptides with antithrombin activity obtainable from extracts of tissues or secretions of leeches of the order Rhynchobdellida, particularly of the species *Theromyzon tessulatum*. The polypeptides have molecular weights of about 14 kD, 9 kD and 3 kD and can be used in pharmaceutical compositions for the treatment of thrombosis related disorders and events.

22 Claims, 6 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
       ( A ) LENGTH: 14 amino acids
       ( B ) TYPE: amino acid
       ( C ) STRANDEDNESS: single
       ( D ) TOPOLOGY: linear ( i i ) MOLECULE TYPE: peptide ( v ) FRAGMENT TYPE: N-terminal ( v i ) ORIGINAL SOURCE:
       ( A ) ORGANISM: Theromyzon tessulatum ( x i ) SEQUENCE DESCRIPTION: SEQ ID NO:1:

```
       Glu  Asp  Asp  Asn  Pro  Gly  Pro  Pro  Arg  Ala  Cys  Pro  Gly  Glu
        1              5                        10
```

( 2 ) INFORMATION FOR SEQ ID NO:2:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( v i ) ORIGINAL SOURCE:
        ( A ) ORGANISM: Theromyzon tessulatum ( x i ) SEQUENCE DESCRIPTION: SEQ ID NO:2:

```
       Ser  Glu  Leu  Gly  Gln  Ser  Cys  Ser  Lys  Glu  Asn  Pro  Cys  Pro  Ser  Asn
        1              5                        10                       15

Met  Lys  Cys  Asn  Arg  Glu  Thr  Phe  Lys
                 20                        25
```

THROMBIN INHIBITORS

BACKGROUND OF THE INVENTION

The present invention relates to novel thrombin inhibitors and, in particular, thrombin inhibitors derived from leech tissue and leech secretions.

Thrombin catalyzes the formation of fibrin clots and inhibits, therefore, the coagulation of blood. Moreover, thrombin has several other bioregulatory roles such as the direct activation of platelet aggregation and the activation of inflammatory response by stimulating the synthesis of platelet activating factor (PAF) by endothelial cells. That means that thrombin plays a central role in thrombosis related disorders such as cardiovascular desease, for example.

Consequently, there is a great interest in a continual search for new or improved thrombin inhibotors and anticoagulants, respectively.

Examples of well known thrombin inhibitors are heparin and hirudin.

Heparin accelerates the anticoagulant activity of antithrombin III. It has been widely used to treat conditions, such as venous thromboembolism, in which thrombin activity is responsible for the development or expansion of a thrombus. It is not effective for therapy in the cases where antithrombin III is decreased, for example in the cases of thrombosis associated with nephrosis or disseminated intravascular coagulation syndrome (DIC). Moreover, heparin produces many undesirable side effects, including hemorrhaging and thrombocytopenia.

Hirudin is a well known and well characterized polypeptide, which is known to be specific for thrombin, and which may be isolated from extracts of the salivary gland and other tissues of leeches of the species *Hirudo medicinalis*. Hirudin and its derivatives are also obtainable by recombinant techniques. The polypeptide has a relatively low molecular weight of 7000 D and is comprised of 65 amino acids. The amino acid sequence of hirudin was first determined by Dodt et al. (FEBS Letters, 165, 180–184, 1984). Three major variants of hirudin (HV1, HV2, HV3) have been found in the medicinal leech *Hirudo medicinalis* and differ in only about 10% of the total amino acid positions. The most notable difference is at the first two positions of the N-terminal end of the molecule: Val-Val in hirudin variant 1 (HV1) and Ile-Thr in hirudin variant 2 (HV2). These differences are of minor nature and do not affect the function nor the specificity of hirudin-thrombin interaction. Hirudin is a potent natural inhibitor of coagulation. It has demonstrated efficacy in preventing venous thrombosis, vascular shunt occlusion and thrombin-induced disseminated intravascular coagulation, but shows, however, prolonged bleeding times.

Phylogenetically, the medicinal leech *Hirudo medicinalis* is a member of the sub-family Hirudininae of the leech familiy Hirudinidae (R. T. Sawyer: "Leech Biology and Behaviour", Oxford University Press, Vol. 2, p.688, 1986). An evolutionarily more advanced leech species is *Hirudinaria manillensis*, which belongs to the sub-family Hirudinariinae of the same family Hirudinidae. Unexpectedly, a related but distinctly quite different isoform of hirudin was discovered recently in Hirudinaria manillensis as described in PCT patent application WO 90/05143. This isoform differs in nearly 40% of the amino acid positions when compared with hirudin from *Hirudo medicinalis*. The two species mentioned above, namely *Hirudo medicinalis* and *Hirudinaria manillensis*, belong to the leech order Arhynchobdellida ("jawed leeches"). In addition to the order Arhynchobdellida, there is one other major order of leeches, i.e. Rhynchobdellida ("proboscis leeches") (R. T. Sawyer: "Leech Biology and Behaviour", Oxford University Press, Vol. 2, p.651, 1986). The best studied member of the order Rhynchobdellida, with respect to salivary proteins, is the "Amazon leech", *Haementeria ghilianii*.

It has been demonstrated that this species, unexpectedly, does not contain an antithrombin (Budzynski et al.: Proc. Soc. Exp. Biol. Med, 168, 259–265, 1981 ). Instead, *Haementeria ghilianii* contains a fibrinogenolytic enzyme called Hementin (US Patent 4390630), as well as an inhibitor of the blood coagulation factor Xa (C. Condra et al.: Thromb. Haemost., 61,437–441, 1986).

Based on this discovery and subsequent work, it has become generally accepted that antithrombin-like activity is restricted to leeches of the order Arhynchobdellida, whereas antithrombin-like activity is currently thought to be lacking in the order Rhynchobdellida.

Despite the developments discussed above, the need continues to exist for supplying besides heparin and hirudin further anticoagulants and antithrombins, respectively, having increased efficacy in the inhibition of clot formation, thrombin-induced platelet activation or endothelial cell activation, which may be produced in commercially feasible quantities.

SUMMARY OF THE INVENTION

Surprisingly, it has been found that compounds with antithrombin-like activity can be isolated from tissues and secretions of leeches of the order Rhynchobdellida, preferably of the family Theromyzon, and most preferably of the species *Theromyzon tessulatum*, which is called sometimes the "bird leech", because this species has an exceptionally specialised lifestyle in that it sucks blood from nares of aquatic birds.

Therefore, it is an object of the present invention to use leeches of the order Rhynchobdellida, preferably the species *Theromyzon tessulatum*, for preparing thrombin inhibitory compounds.

It has been found that thrombin inhibitory activity can be measured in extracts comprising water soluble components of these leeches. Therefore, it is an object of this invention to prepare an extract with thrombin inhibitory activity from tissue or secretions of leeches of the order Rhynchobdellida or the family Theromyzon or the species *Theromyzon tessulatum* containing water soluble components thereof.

An active thrombin inhibitor could be isolated from the said extracts. Thus, it is an object of the present invention to provide an essentially purified thrombin inhibitor which can be identified as polypeptides having thrombin inhibitory activity obtainable from an extract as defined above and in the claims by purification the extract obtained by homogenization of the anterior third of frozen and lyophilized leeches with water/acetone, by means of thrombin-specific affinity chromatography followed by at least one gel filtration step and at least one reversed phase HPLC step.

The thrombin inhibitor preferably includes active polypeptide fragments with molecular weights of about 3 kD, approximately 9 kD and approximately 14 kD respectively. These active polypeptides may be eventually regarded as degradation products of a parent or precursor thrombin inhibitor.

The thrombin inhibitor according to the present invention is new because it differs from known antithrombins, especially from hirudin, in the molecular weight as well as in the isoelectric point and the N-terminal amino acid sequences, which showed limited homology (below 40%) with other thrombin inhibitors.

Therefore, it is a further object of this invention to isolate from said extract a thrombin inhibitor comprising at least one polypeptide having thrombin inhibitory acvtivity and a molecular weight of about 3 kD.

In addition, it is object of this invention to provide a thrombin inhibitor comprising at least one polypeptide having thrombin inhibitory acvtivity and a molecular weight of about 9 kD and the N-terminal amino acid sequence:

Glu Asp Asp Asn Pro Gly Pro Pro Arg Ala Cys Pro Gly Glu (SEQ. ID. NO:1).

Additionally, it is object of this invention to provide a thrombin inhibitor comprising at least one polypeptide having thrombin inhibitory acvtivity and a molecular weight of about 14 kD and the N-terminal amino acid sequence:

Ser Glu Leu Gly Gln Ser Cys Ser Lys Glu Asn Pro Cys Pro Ser Asn Met Lys Cys Asn Arg Glu Thr Phe Lys (SEQ. ID. NO:2).

According to the invention, the terms "about 3 (9, 14) kD" include a maximum deviation of plus/minus 1 kD, preferably of 0.5 kD. Furthermore, it is an object of the invention to include also said sequences above and below wherein exchanges of amino acids conserving the principal biological properties have ocurred. This also includes variations, fragments, subunits, naturally occurring mutations and randomly generated artificial mutants. Also included are hybrid proteins such as fusion proteins deriving from the disclosed peptides.

The invention relates, in addition, to a process for manufacturing an extract as defined above and in the claims by homogenizing tissue or secretions of leeches of the order Rhynchobdellida, preferably of the species *Theromyzon tessulatum*, and preparing a fraction comprising water soluble components thereof.

Furthermore, it is an object of the present invention to provide a process for manufacturing a polypeptide according to claims 4 to 7 by purifying said extract by means of thrombin specific affinity chromatography and at least one further standard chromatography step.

The thrombin inhibitor according to the invention has anticoagulant and antithrombotic properties. It may therefore be used in all clinical states, where the coagulation system is affected. These uses include treatment of thrombosis, stroke, myocardial infarction, deep venous thrombosis, obstruction of limb arteries, pulmonary thrombosis, retinal artery thrombosis or any other thrombotic events. Furthermore, the thrombin inhibitor(s) can be used for patients with arteriovenous shunts, or undergoing coronary bypass surgery. The polypeptides according to this invention may also be used as anticoagulant in the prophylaxis of thrombosis or arterial reocclusions, for the conservation of blood or blood products and for extracorporeal blood or plasma circulations.

The thrombin inhibitor (polypeptides) according to the invention show(s) a biological activity which is comparable with hirudin in principal. The binding affinity to thrombin (inhibitory constant) is even slightly increased compared with hirudin which is known as the strongest thrombin inhibitor up to now.

Thus, it is an additional object of this invention to provide the polypeptides defined above and in the claims for use as a medicament, particularly for the in vivo treatment of thrombosis related disorders and for inhibiting platelet aggregation and blood clots in extracorporeal blood.

Finally, there is further provided by the present invention a pharmaceutical composition comprising a thrombin inhibitor or a polypeptide as defined above, respectively, and a pharmaceutically acceptable carrier for the treatment of thrombosis related disorders as mentioned above.

BRIEF DESCRIPTION OF THE FIGURES

Details of the figures are explained in examples 1 to 10.

DETAILED DESCRIPTION OF THE INVENTION

Figure 1:
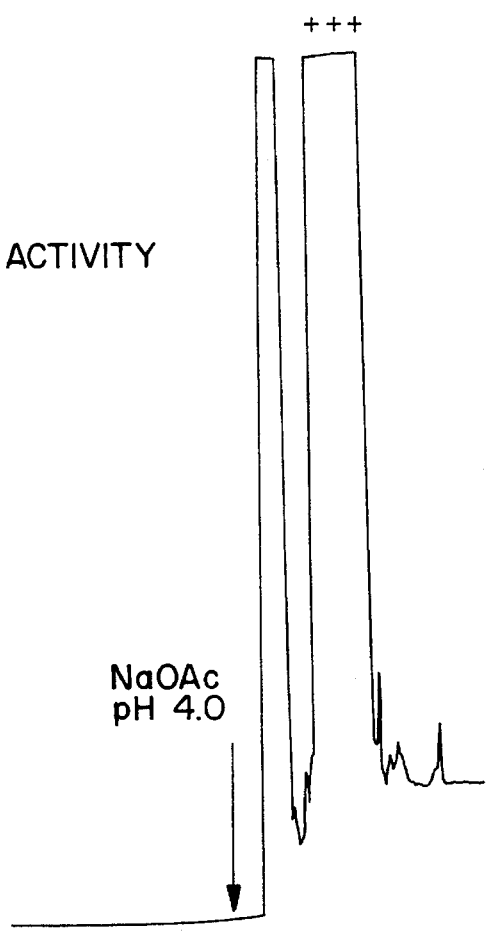
FIG. 1 shows elution profile of antithrombin from affinity column (example 3).

The thrombin inhibitor(s) according to this invention may be isolated and purified from tissues or secretions of leeches of the order Rhynchobdellida, preferably of the family Theromyzon. From Leeches of the family Theromyzon the thrombin inhibitors are obtainable with similar activitiy and only minor differences. Examples for suitable species of the family Theromyzon are *T. binannulatum, T. cooperi, T. gariaewi, T. maculosum, T. mollissimum, T. pallens, T. propinquum, T. rude, T. sexoculatum*, and particularly *T. tessulatum*.

Preferably, the salivary glands of the leeches are used as source according to the invention. However, because it takes effort to prepare the salivary glands, and a considerable loss of material cannot be prevented it is also possible to use the heads or the anterior third of the leeches as source.

Typically, the first step of the method comprises preferably substantial freezing and/or freeze-drying of the leech tissue prior to homogenization which is typically carried out in acetone or acetone/water mixtures. However, other polar organic solvents can be used in order to remove non-water soluble components. It is further preferred that the extract obtained by step one is subjected to centrifugation prior to affinity chromatography to remove unwanted cell debris. It is preferred that the affinity chromatography employs a column provided with "thrombin active sites". The term "thrombin active sites" as used herein denotes the presence of thrombin sites at the column to which a thrombin inhibitor can adhere. Examples for thrombin active sites are immobilized native or desactivated thrombin also including thrombin-derived peptides, peptidomimetica or other thrombin derivatives. According to the invention, thrombin or said thrombin derivatives are immobilized to an active gel matrix preferably by reacting with an azlacton group of said gel matrix according to known methods. Otherwise, affinity chromatograpy was done by standard techniques.

It is preferred that the method of gel filtration is used together with affinity chromatography. The gel matrix according to the invention has an exclusion limit of about 5 kD, and, therefore, allows for fractioning in the range of approximately 1 kD and 5 kD.

It is preferred that the isolated antithrombin extracts are further subjected to reversed phase HPLC for further purification. Polypeptide fragments as hereinbefore described are obtainable by purification of the isolated extracts by RP-HPLC. Examples for suitable reversed phase materials are silica gels modified with C2–C18 aliphatic substituents. However, the polypeptides according to this invention can be purified by other well known chromatographic procedures. Details of the HPLC purification are given in the examples.

Activity of thrombin inhibitors in the ectracts and in the specific fractions of the purificaton steps may be measured in vitro by prolongation of clotting time (F. Markwardt: Meth. Enz., 19, 924–932, 1970) or by the reduction of the cleavage of an thrombin specific chromogenic substrate such as Tosyl-glycyl-prolyl-arginine-4-nitroanilide acetate (Chromozym TH, Boehringer Mannheim) as described (H. U. Bergmeyer: Meth. Enz. Anal., 3rd Ed., Vol. 5, 365–394, 1988).

As indicated above, the polypeptides according to the present invention are suitable as pharmaceutically effective compounds in parmaceutical compositions and combinations.

The pharmaceutical formulations according to the invention optionally may comprise additional active incredients like anti-coagulants such as hirudin or heparin or thrombolytic agents such as plasminogen activator or hementin.

The novel polypeptides and thrombin inhibitors, respectively, according to the invention may form pharmaceutically acceptable salts with any non-toxic, organic or inorganic acid. Inorganic acids are, for example, hydrochloric, hydrobromic, sulphuric or phosphoric acid and acid metal salts such as sodium monohydrogen orthophosphate and potassium hydrogen sulfate. Examples for organic acids are the mono, di and tri carboxylic acids such as acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic and sulfonic acids such as methane sulfonic acid. Salts of the carboxy terminal amino acid moiety include the non-toxic carboxylic acid salts formed with any suitable inorganic or organic bases. These salts include, for example, alkali metals such as sodium and potassium, alkaline earth metals such as calcium and magnesium, light metals of Group IIIA including aluminium, and organic primary, secondary and tertiary amines such as trialkylamines, including triethylamine, procaine, dibenzylamine, 1-ethenamine, N,N'-dibenzylethylene-diamine, dihydroabietylamine and N-alkylpiperidine.

As used herein, the term "pharmaceutically acceptable carrier" means an inert, non toxic solid or liquid filler, diluent or encapsulating material, not reacting adversely with the active compound or with the patient. Suitable, preferrably liquid carriers are well known in the art such as steril water, saline, aqueous dextrose, sugar solutions, ethanol, glycols and oils, including those of petroleum, animal, vegetable, or synthetic origin, for example, peanut oil, soybean oil and mineral oil.

The formulations according to the invention may be administered as unit doses containing conventional non-toxic pharmaceutically acceptable carriers, diluents, adjuvants and vehicles which are typical for parenteral administration.

The term "parenteral" includes herein subcutaneous, intravenous, intra-articular and intratracheal injection and infusion techniques. Also other administrations such as oral administration and topical application are suitable. Parenteral compositions and combinations are most preferably adminstered intravenously either in a bolus form or as a constant fusion according to known procedures. Tablets and capsules for oral administration contain conventional excipients such as binding agents, fillers, diluents, tableting agents, lubricants, disintegrants, and wetting agents. The tablets may be coated according to methods well known in the art.

Oral liquid preparations may be in the form of aqueous or oily suspensions, solutions, emulsions, syrups or elixirs, or may be presented as a dry product for reconstitution with water or another suitable vehicle before use. Such liquid preparations may contain conventional additives like suspending agents, emulsifying agents, non-aqueous vehicles and preservatives.

Topical applications may be in the form of aqueous or oily suspensions, solutions, emulsions, jellies or preferably emulsion ointments.

Unit doses according to the invention may contain daily required amounts of the protein according to the invention, or sub-multiples thereof to make up the desired dose. The optimum therapeutically acceptable dosage and dose rate for a given patient (mammals, including humans) depends on a variety of factors, such as the activity of the specific active material employed, the age, body weight, general health, sex, diet, time and route of administration, rate of clearance. the object of the treatment, i.e., therapy or prophylaxis and the nature of the thrombotic desease to be treated, antiplatelet or anticoagulant activity.

Therefore, in compositions and combinations useful as anticoagulants in a treated patient (in vivo) a pharmaceutical effective daily dose of the peptides of this invention is between about 0.01 and 100 mg/kg body weight, preferably between 0.1 and 10 mg/kg body weight According to the application form one single dose may contain between 0.5 and 10 mg of the thrombin inhibitor To achieve an anticoagulant effect in extracorporeal blood a pharmaceutically effective amount of the inventive peptides is between 0.2 and 150 mg/l, preferably between 1 mg and 20 mg/l extracorporeal blood.

It is also object of this invention to provide an implantable or extracorporal medical device for use in contact with body fluids in order to render the device surface substantially thromboresistant, coated with an immobilized polypeptide as defined above and in the claims. The polypeptide according to the invention is immobilzed on a medical device so as to render the surface biocompatible and thromboresistant. Such devices sometimes have wettable surfaces which typically induce platelet aggregation, which is a disadvantage in their intended uses in inplantable and extracorporeal devices in contact with blood or other body fluids. Example for such devices which are commonly made from plastics materials and synthetic fibres are protheses, artificial organs, sutures, artificial vascular segments, catheters, dialysers, tubes and vessels carrying blood.

The present invention will now be further illustrated with reference to the following examples which are for the purpose of illustration and do not limit the scope of the invention.

EXAMPLE 1

Demonstration of the Presence of Antithrombin in *T. tessulatum*

Ten heads of *Theromyzon tessulatum* were homogenized in isotonic saline. The homogenate was briefly centrifuged to remove particulate matter and the supernatant kept to carry out the following antithrombin assay, along with other haematological tests as indicated.

For estimation of antithrombin activity 20 µl of the above mentioned extract were mixed with 10 µl thrombin (1 U). To this mixture 100 µl of a 0.5 mg/ml fibrinogen solution were added, further mixed and incubated at 37° C. for 1 min.

Further details of this assay have been described by R. T. Sawyer et al. (Comp. Haematol. Int., 1, 35–41, 1991). The following table summarizes the in vitro inhibition of clotting parameters with crude extracts from *Theromyzon tessulatum*:

Table 1: Demonstration of the presence of antithrombin activity in *T. tessulatum*

|  | normal controls [sec] | crude extract [sec] |
| --- | --- | --- |
| Prothrombin Time (extrinsic) | 15 | 42 |
| Activated PTT (intrinsic) | 40 | 220 |
| Thrombin Time (antithrombin) | 45 | >600 |
| Reptilase Time | 20 | 20 |

It can be seen from the above data that the head region of *Theromyzon tessulatum* contains a water-soluble factor or factors which significantly prolong the thrombin clotting time.

EXAMPLE 2

Chromogenic Assay for Thrombin- and Factor Xa-Inhibition a) Thrombin-Inhibition 20 µl thrombin solution (5 NIH-U thrombin/ml of 250 mM phosphate buffer containing 0.05% PEG 6000 pH 6.5) was preincubated with 880 µl thrombin assay buffer (100 mM Tris-HCl, 200 mM NaCl, 0.05% PEG pH 8.3) in a photometer cuvette for 5 min at room temperature. Reaction was started by addition of 100 µl substrate solution (4 mg Chromozym TH from Boehringer, Mannheim, Germany dissolved in 5 ml $H_2O$) and the absorption read at 405 nm for 5 min with 30 sec interval at 25° C.

For measurement of inhibition activity 10–200 µl sample or hirudin as standard were mixed with 20 µl thrombin solution and were made to 900 µl total volume with assay buffer. This mixture was preincubated for 5 min at room temperature and reaction was started by addition of 100 µl substrate solution.

b) Inhibition of Factor Xa Activity

20 µl factor Xa solution (10 U/0.5 ml diluted to 2.0 ml with $H_2O$) was preincubated with 880 µl factor Xa assay buffer (100 mM Tris-HCl, 200 mM NaCl, 0.05% PEG pH 8.3) in a photometer cuvette for 5 min at room temperature. Reaction was started by addition of 100 µl substrate solution (3.5 mg Chromozym X from Boehringer, Mannhelm dissolved in 5 ml $H_2O$) and the absorption read at 405 nm for 5 min with 30 sec interval at 25° C.

For measurement of inhibition activity 10–200 µl sample were mixed with 20 µl factor Xa solution and were made to 900 µl total volume with assay buffer. This mixture was preincubated for 5 min at room temperature and reaction was started by addition of 100 µl substrate solution.

EXAMPLE 3

Purification of Thrombin Inhibitor from *Theromyzon tessulatum*

Step 1

The anterior third of 1000 second fed *Theromyzon tessulatum* were immediatedly frozen at −70° C. and lyophilized. To this material 35 ml 40% acetone was added and the suspension was homogenized in an ultra-torax 3× for 10 sec each. Treatment for 2 min in a sonicator was followed by an additional homogenization step (30 sec). The homogenate was centrifuged for 15 min at 6000 rpm and the resulting supernatant saved (S1).

To the pellet 1 was added another 35 ml 40% acetone and a second homogenization was performed (1×10 sec; 2 min sonication; 1×30 sec). The homogenate was again centrifuged for 15 min at 6000 rpm.

Supernatant 2 was added to the saved supernatant 1, to the combined supernatants was added 80% acetone (vol/vol).

The pH was adjusted to 4.0 with acetic acid and the resulting suspension centrifuged at 6000 rpm for 20 min. The pellet 3 was discarded. The supernatant 3 was concentrated 4-fold by means of a rotary evaporator (Speed Vac).

The acetone-free extract was tested positive for antithrombin activity in the clotting assay according to example 1 as well as in the chromogenic assay according to example 2.

Step 2

The acetone-free extract was applied to a PD-10 column (Pharmacia) for buffer exchange. The column was equilibrated with affinity buffer (20 mM Tris-HCl, 50 mM NaCl pH 7.4) and 2.5 ml of the extract from step 1 was applied to the column. The eluate was tested for antithrombin activity.

The thrombin affinity column was prepared in the following way:

400 mg dry Azlacton Tentacle Fractogel matrix (E. Merck, Darmstadt, Germany) was suspended in 7 ml of coupling buffer (50 mM phosphate, 150 mM NaCl pH 7.5) for 2 hrs at room temperature. The suspension was washed twice by centrifugation and resuspension in coupling buffer. 5000 NIH-U bovine thrombin (Sigma) were dissolved in 1 ml $H_2O$ and the pH adjusted to 7.5. This thrombin solution was equilibrated to coupling buffer by means of PD-10 gel filtration. To the equilibrated thrombin solution was added sodium sulfate to reach a final concentration of 1M. Thrombin protein was pipetted immediately to the activated gel matrix and coupling was allowed for 3 hrs at 4° C. with gentle mixing. Washing was done 3× with 5 volumes of coupling buffer each. For desactivation of the matrix 1.5 ml ethanolamine was added and left overnight at 4° C. with gentle shaking. The matrix was washed twice with 5 volumes acetate buffer (100 mM Na-acetate, 500 mM NaCl pH 4.0). Final equilibration was done by washing twice with 5 volumes of affinity buffer.

Active eluates from PD-10 column were loaded onto the affinity column by means of a persistaltic pump (flow 10 ml/hr). The non-bound fraction was collected and the column washed with 12 ml affinity buffer (wash 1 ). Elution was performed with 6 ml acetate buffer pH 4.0 and fractions of 0.5 ml volume collected. The elution profile from this column is depicted in FIG. 1.

First elution was followed by a second step using 6 ml acetate buffer pH 3.0. Fractions of 1.5 ml were collected. The column was reequilibrated with 25 ml affinity buffer.

The results of the extraction and affinity step are summarized in the following table 2:

TABLE 2

Results of affinity purification of thrombin inhibitor from Theromyzon tessulatum (affi = affinty chromatography)

| fraction | volume [ml] | clotting time [sec] | thrombin inhib. [IU] | F Xa inhib. [IU] |
| --- | --- | --- | --- | --- |
| blank | — | 20.5 | 0 | 0 |
| acetone extract | 34 | 59.4 | 33 | n.d. |
| non-bound affi | 34 | 24.3 | 1.8 | 1.1 |
| wash 1 | 24 | 20.2 | 1.6 | 1.0 |
| affi eluate 1 | 4 | >600 | 25 | 0.2 |
| affi eluate 2 | 4 | 22.1 | 0 | 0 |

EXAMPLE 4

Gel filtration Analysis of Active Thrombin Inhibitor from Theromyzon tessulatum

Active material was applied to a Biogel P4 gel filtration column (Biorad) which had a volume of 25 ml. Elution was done with 20 mM Tris-HCl, 50 mM NaCl pH 7.4 at a flow rate of 4 ml/hr. Fractions of 1 ml were tested for their antithrombin activity.

Figure 2:
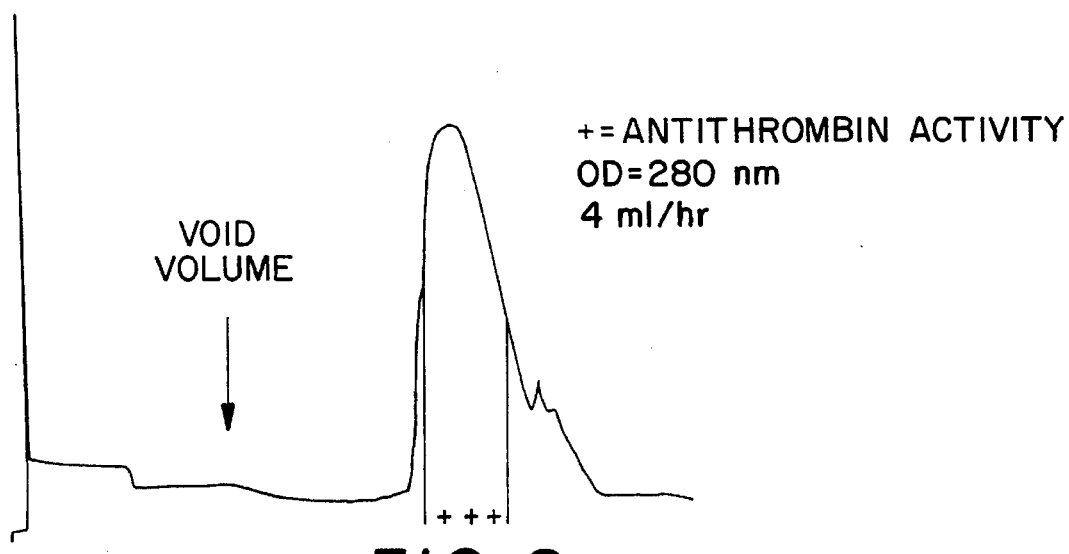
FIG. 2 shows gel filtration analysis of antithrombin derived from T. tessulatum on Biogel P4 (example 4).

The P4 gel matrix has a exclusion limit of 5000 D and allows for fractioning in the range of 1000 to 5000 D molecular weight. Suprisingly, it was found, that antithrombin activity elutes in the fractionation volume, i.e. has an apparent molecular weight below 5000 D (FIG. 2). This behaviour is in contrast to hirudin (molecular weight 7000 D) which appears in the exclusion volume under the same conditions. From calibration of the P4 column a molecular weight of approximately 3000 D was calculated for the antithrombin activity from *Theromyzon tessulatum*.

EXAMPLE 5

Reversed Phase-HPLC of Purified Thrombin Inhibitor from *Theromyzon tessulatum*

Active eluates after the affinity chromatography step according to example 3 were further analyzed by RP-HPLC. 20 μl of sample was injected on a HPLC column (LiChrospher 300 RP-18, 5 μm; E. Merck, Darmstadt, Germany) and eluted with the following acetonitrile gradient at 1.0 ml/min:

Buffer A: 0.1% trifluoracetic acid in $H_2$)

Buffer B: 0.08% trifluoracetic acid in acetonitrile

Gradient: 0–2 min 10% B

2–3 min Inject

3–28 rain 60% B

Figure 3:
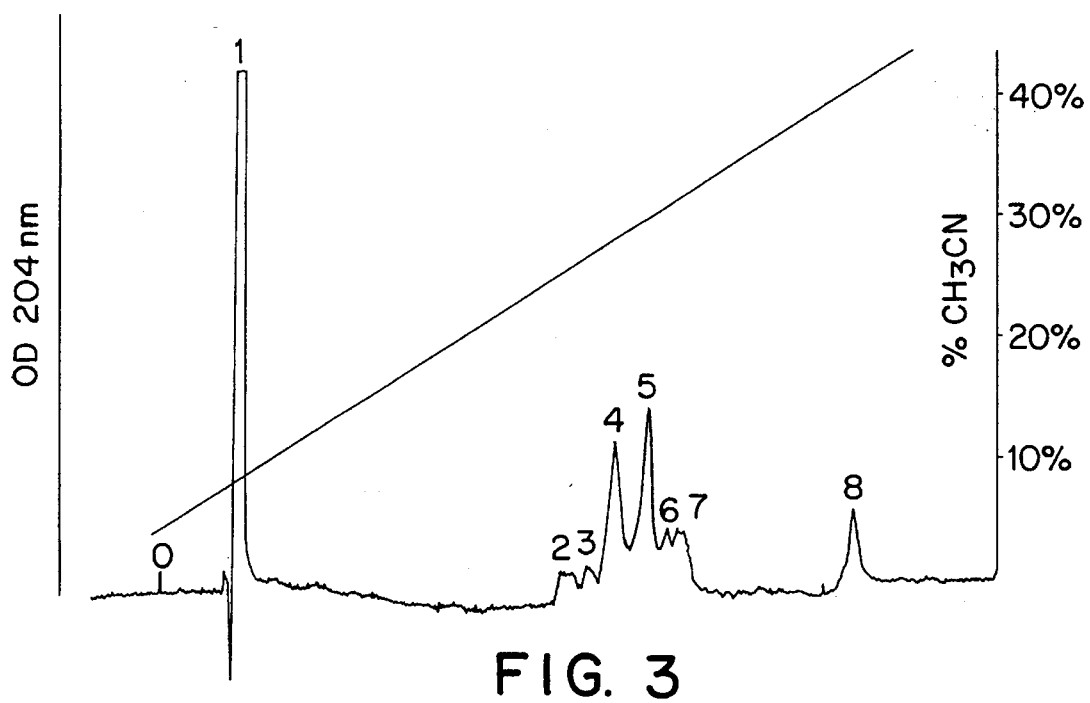
FIG. 3 shows analytical RP-HPLC of positive fractions from affinity step (example 5).

FIG. 3 depicts a typical analytical chromatographic trace recorded at 220 nm. Thrombin inhibition activity was found in the peaks labelled as peak 2 and peak 4. The information from analytical HPLC runs was subsequently used to perform preparative separations under the same conditions.

Figure 4:
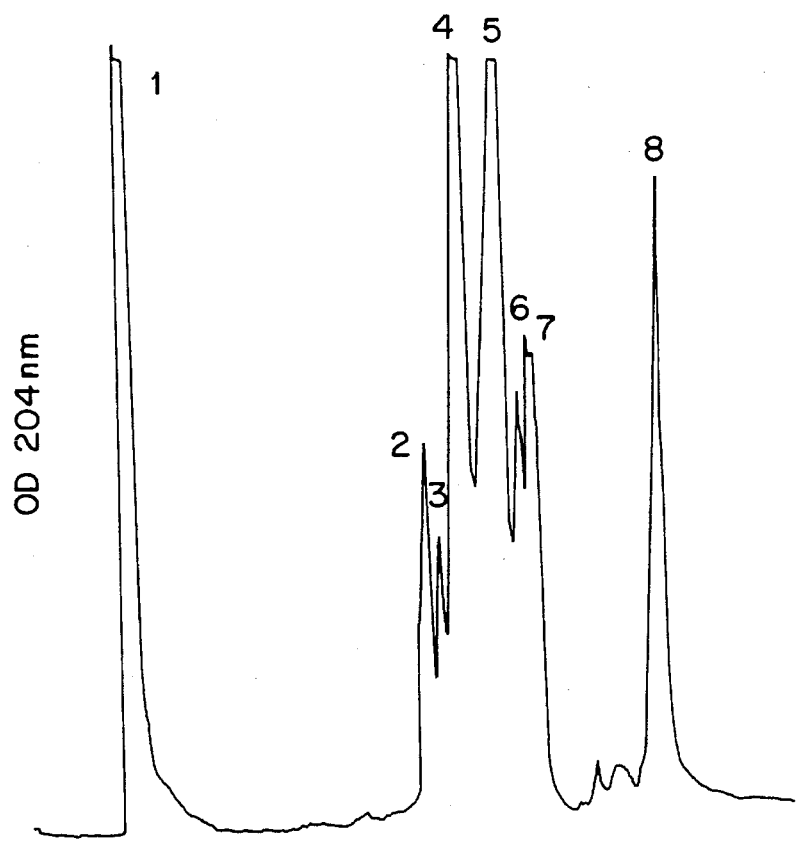
FIG. 4 shows preparative RP-HPLC of positive fractions from affinity step (example 5).

Preparative purifications were run with aliquots of 500 μl sample from affinity chromatography (FIG. 4). Individual peaks were collected, pooled and concentrated by rotary evaporation in a Speed Vac. Dried fractions were reconstituted in $H_2O$ and assayed for antithrombin activity in the clotting time test as well as in the chromogenic assay described in example 2.

Major activities in both test systems were found in peaks 2 and 4, with some activity also in peak 5, which most probably reflects contamination of peak 4 in the peak 5 material. All other peaks of the chromatogramm showed no thrombin inhibition activity at all. The sum of activity of peak 2 and 4 accounted for approximately 93% of total activity.

EXAMPLE 6

Figure 5:
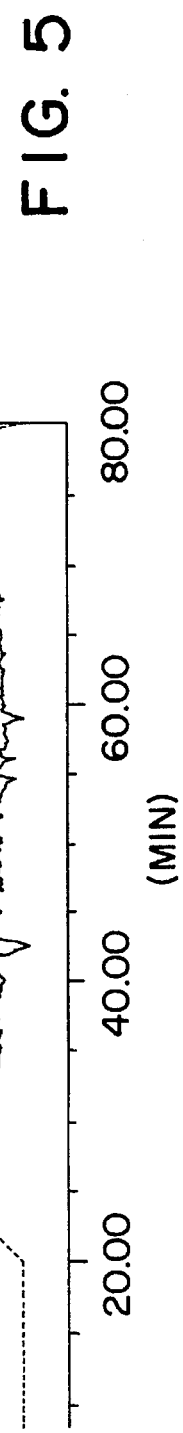
FIG. 5 shows comparison of hirudin and inihibitor according to this invention on HPLC (example 6).

Comparison of Thrombin Inhibitor According to Present Invention with Hirudin on HPLC To demonstrate further that the inhibitor according to this invention is a fundamentally different molecule from hirudin the following experiment was conducted. To the active peak 2 after HPLC according to example 5 was added a similar protein concentration of purified hirudin and the mixture was subjected to RP-HPLC in an acetonitrile gradient (40–70%). Two peaks were found which contain antithrombin activity (FIG. 5). From comparison runs, where the single inhibitors have been injected, the assignment of peaks as indicated in FIG. 5 could be made.

From FIG. 5 it is clear, that the antithrombin according to this invention elutes at a position very different from that of hirudin. The same could be demonstrated for the active peak 4 after HPLC separation according to example 5.

EXAMPLE 7

Further Characterization of Peak 2 with Antithrombin Activity

Purity

Figure 6:
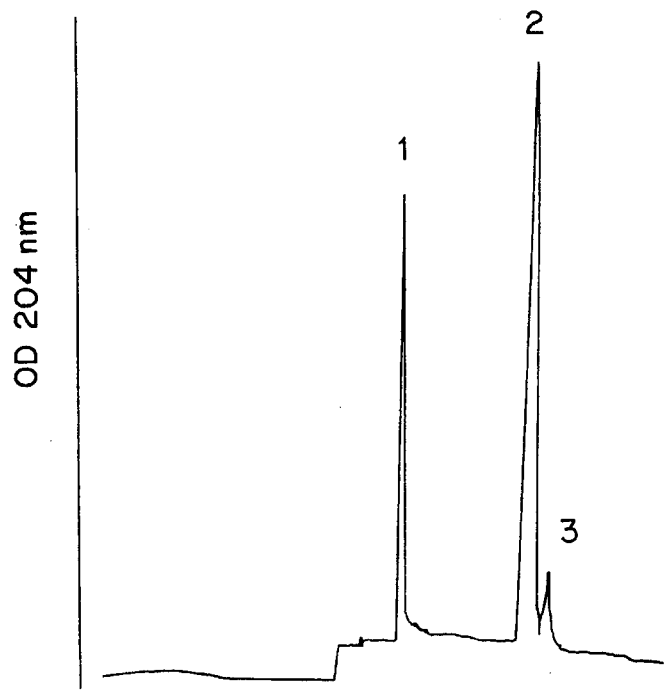
FIG. 6 shows rechromatography of active peak 2 from RP-HPLC (example 7).
Figure 8:
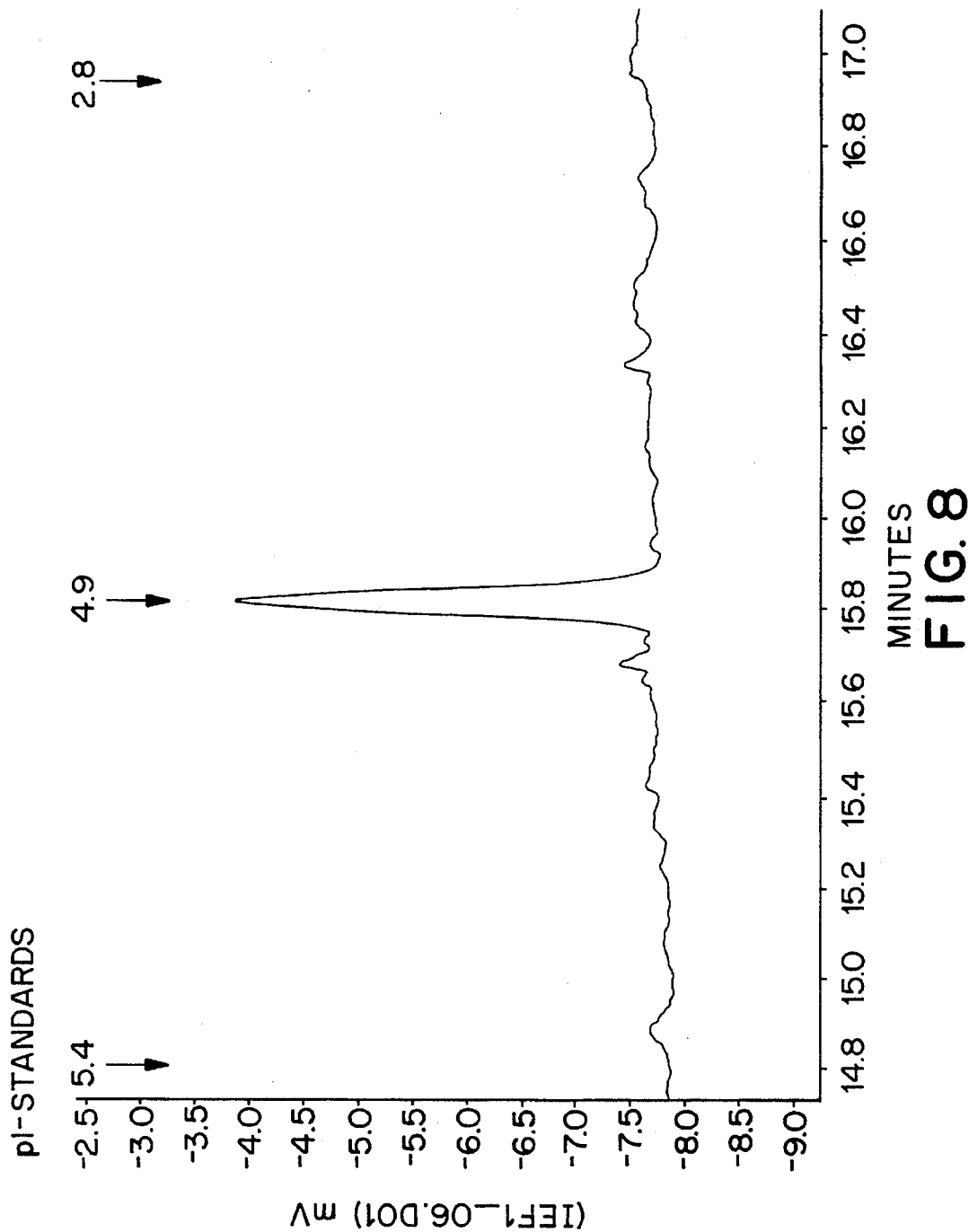
FIG. 8 shows IEF trace of active peak 2 from RP-HPLC (example 7)

Pooled active peak 2 from RP-HPLC was subjected to rechromatography under the same conditions like the one in FIG. 3. As shown in FIG. 6 a small amount of contaminating material could still be separated from the major active peak, resulting in a homogenous preparation after the second RP-HPLC (see also FIG. 8, which shows capillary electrophoresis of this fraction).

Thrombin inhibition

Peak 2 from RP-HPLC was active in the clotting assay (thrombin time >600 sec/5 μl) as well as in the chromogenic antithrombin test according to example 2. Activity in the latter assay was 3.2 IU/250 μ l. Factor Xa inhibition activity could not be detected in peak 2 using the assay described in example 2, reflecting a maximal anti-FXa activity of <<1% of the antithrombin activity. Therefore it is concluded, that the inhibitor disclosed herein is very specific for thrombin.

Active site titration

The inhibitor constant against thrombin was determined by spectrofluorometric titration of standardized thrombin solution with the inhibitor according to this invention. Details of the method have been described elsewhere by G. W. Jameson et al. (Biochem. J., 131,107–117, 1973).

Briefly the fluorogenic substrate Tos-Gly-Pro-Arg-AMC was used in a concentration of 50 μM in the titration experiments. Assays were performed in 100 mM Tris-HCl, 200 mM NaCl, 0.05% PEG 6000 pH 7.8 at 25° C. A concentration of 20 pM active site titrated human α-thrombin thrombin was incubated with the inhibitor at 0.2–5 $\times E_0$ for 10 min and steady velocities were measured after addition of substrate. The kinetic constants were determined using the nonlinear regression analysis program GraFit (R. J. Leatherbarrow, Erithacus Software, Staines, UK, 1980). The $K_i$ was found to be 178 femtomolar.

Molecular Weight

Figure 7:
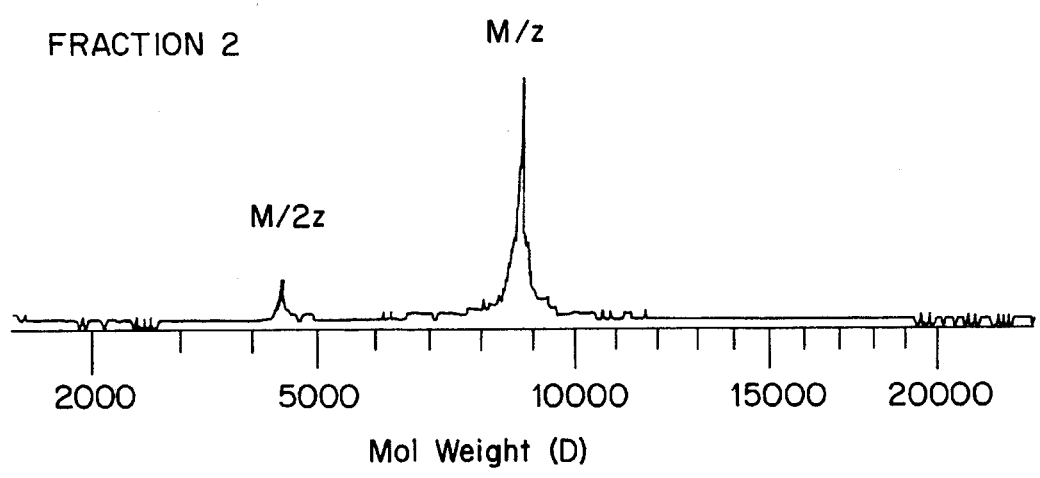
FIG. 7 shows mass spectrum of active peak 2 from RP-HPLC (example 7).

The molecular weight of active peak 2 was determined by laser desorption mass spectrometry using the MALDI-TOF method (Kratos). 0.5 μl of sample was mixed with a few μl of dihydroxybenzoic acid in acetonitrile which serves as matrix. The mixture was dried under cold air on a silver sample holder and placed into the instrument. The resulting mass spectrum was calibrated with standard proteins of known molecular weight. The peak corresponded to a molecular mass of about 9000 D (FIG. 7).

Isolelectric Focussing

The isoelectric point of the inhibitor was measured by capillary electrophoresis in the IEF mode (Applied Biosystems). As could be seen from to FIG. 8 the inhibitor peak appeared at a pl of 4.9 as compared to standard proteins.

EXAMPLE 8

Sequence Data of Peak 2 with Antithrombin Activity

Following N-terminal sequence was obtained with the peak 2 from RP-HPLC (example 5) by standard edman degradation chemistry on a Beckman Peptide Sequencer:

Glu Asp Asp Asn Pro Gly Pro Pro Arg Ala Cys Pro Gly Glu (SEQ. ID. NO:1).

EXAMPLE 9

Further Characterization of Peak 4 with Antithrombin Activity

Purity

Figure 9:
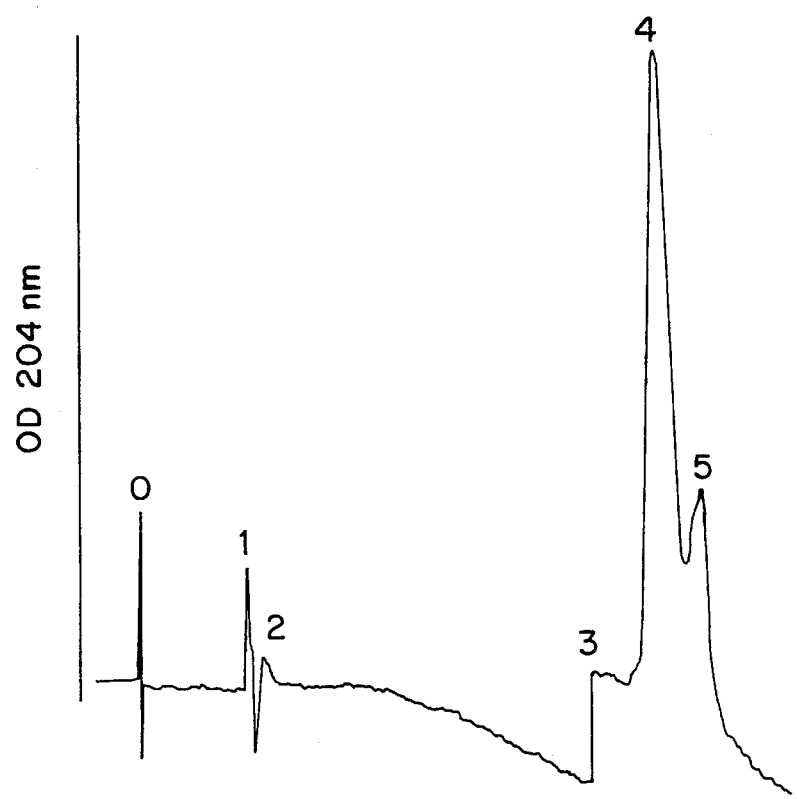
FIG. 9 shows rechromatography of active peak 4 from RP-HPLC (example 9)

Pooled active peak 4 from RP-HPLC was subjected to rechromatography under the same conditions. As shown in FIG. 9 some contaminating material could still be separated from the major active peak, resulting in a homogenous preparation after the second RP-HPLC.

Thrombin inhibition

Peak 4 from RP-HPLC was active in the clotting assay (thrombin time >600 sec/5 μl) as well as in the chromogenic antithrombin test according to example 2. Activity in the latter assay was 1.3 IU/250 μl. Factor Xa inhibition activity could not be detected in peak 2 using the assay described in example 2, reflecting a maximal anti-FXa activity of <<1% of the antithrombin activity. Therefore it is concluded, that the inhibitor disclosed herein is very specific for thrombin.

Active site titration

The inhibitor constant against thrombin was determined by spectrofluorometric titration of standardized thrombin solution with the inhibitor according to this invention. For details see example 7. The $K_i$ was found to be 240 femtomolar.

Molecular Weight

Figure 10:
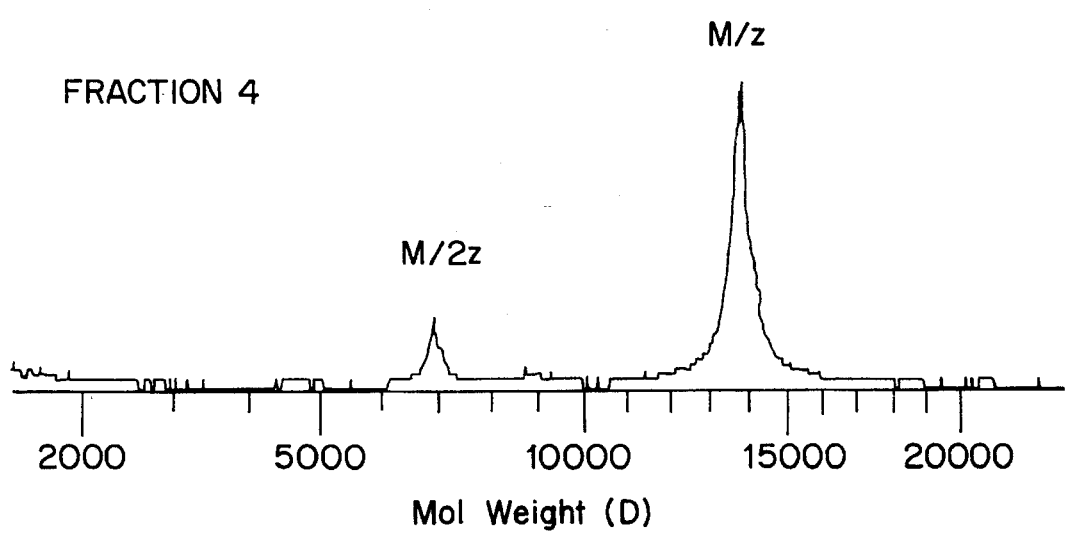
FIG. 10 shows mass spectrum of active peak 4 from RP-HPLC (example 9)

The molecular weight of active peak 4 was determined by laser desorption mass spectrometry using the MALDI-TOF method (Kratos) as described in example 7. The resulting mass spectrum was calibrated with standard proteins of known molecular weight. The peak corresponded to a molecular mass of about 14 kD (FIG. 10).

EXAMPLE 10

Sequence Data of Peak 4 with Antithrombin Activity

Following N-terminal sequence was obtained with the peak 4 from HPLC (example 5) by standard edman degradation chemistry on a Beckman Peptide Sequencer:

Ser Glu Leu Gly Gln Ser Cys Ser Lys Glu Asn Pro Cys Pro Ser Asn Met Lys Cys Asn Arg Glu Thr Phe Lys (SEQ. ID. NO:2).

EXAMPLE 11

Using the same procedure as described in examples 1–5, polypeptides with antithrombin activity could also be isolated from the following Theromyzon species:

T. binannulatum,

T. cooperi,

T. garjaewi,

T. maculosum,

T. sexoculatum.

We claim:

1. An extract containing water soluble components of tissue or secretions of a leech of the order Rhynchobdellida, family Theromyzon, having thrombin inhibitory activity.

2. A process for preparation of an extract of claim 18, comprising homogenizing tissue or secretions of a leach of the order Rhynchobdellida, family Theromyzon, and isolating an extract comprising water soluble components having thrombin inhibitory activity.

3. A process of claim 2, wherein the extract is obtained by homogenizing the anterior third of frozen and lyophilized leeches with water/acetone.

4. A purified polypeptide or polypeptide composition having thrombin inhibitory activity obtainable from an extract of claim 1, further purified from the extract obtained by homogenizing tissue or sectetions of leeches with water/acetone, wherein the purification steps comprise:

thrombin-specific affinity chormatography, followed by
        at least one gel filtration step and
        at least one reversed phase high performance liquid chromatograhpy step.

5. The extract of claim 1, wherein the leech is of the species *Theromyzon tessulatum.*

6. The extract of claim 1, obtained by homogenizing the anterior third of frozen and lyophilized leeches with water/acetone.

7. A purified polypeptide or polypeptide composition having thrombin inhibitory activity obtainable from the extract of claim 1, purified from the extract obtained by homogenizing the anterior third of frozen and lyophilized leeches with water/acetone, wherein the purification steps comprise:

thrombin-specific affinity chromatography, followed by
        at least one gel filtration step and
        at least one reversed phase high performance liquid chromatography step.

8. The purified polypeptide or polypeptide composition of claim 7, wherein at least one polypeptide has a molecular weight of about 3 kD.

9. A pharmaceutical composition comprising an effective amount of the polypeptide of claim 8, and a pharmaceutically acceptable excipient.

10. The purified polypeptide or polypeptide composition of claim 7, wherein at least one polypeptide has a molecular weight of about 9 kD.

11. A pharmaceutical composition comprising an effective amount of the polypeptide of claim 10, and a pharmaceutically acceptable excipient.

12. The purified polypeptide of claim 10, having the N-terminal amino acid sequence of SEQ ID NO:1.

13. A pharmaceutical composition comprising an effective amount of the polypeptide of claim 12, and a pharmaceutically acceptable excipient.

14. The purified polypeptide or polypeptide composition of claim 7, wherein at least one polypeptide has a molecular weight of about 14 kD.

15. A pharmaceutical composition comprising an effective amount of the polypeptide of claim 14, and a pharmaceutically acceptable excipient.

16. The purified polypeptide of claim 14, having the N-terminal amino acid sequence of SEQ ID NO:2.

17. A pharmaceutical composition comprising an effective amount of the polypeptide of claim 16, and a pharmaceutically acceptable excipient.

18. A pharmaceutical composition comprising an effective amount of the polypeptide of claim 7, and a pharmaceutically acceptable excipient.

19. A method of treating a thrombosis-related disease, comprising administering to a patient in need thereof an effective amount of the polypeptide of claim 7.

20. A method of inhibiting platelet aggregation in extracorporeal blood, comprising admixing an effective amount of the polypeptide of claim 7 with extracorporeal blood.

21. A process for preparation of polypeptide of claim 7, comprising:

homogenizing tissue or secretions of a leech of the order *Rhynchobdellida,* family *Theromyzon;* isolating an extract comprising water soluble components having thrombin inhibitory activity; and purifying the extract by:
        thrombin-specific affinity chromatography, followed by
        at least one further chromatography step.

22. A process of claim 21, wherein the exact is obtained by homogenizing the anterior third of frozen and lyophilized leeches with water/acetone.

\* \* \* \* \*